US007775368B2

(12) United States Patent
Schwartz et al.

(10) Patent No.: US 7,775,368 B2
(45) Date of Patent: Aug. 17, 2010

(54) MICRO-CHANNEL LONG MOLECULE MANIPULATION SYSTEM

(75) Inventors: David Charles Schwartz, Madison, WI (US); Eileen T. Dimalanta, Madison, WI (US); Juan J. de Pablo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1221 days.

(21) Appl. No.: 10/688,416

(22) Filed: Oct. 17, 2003

(65) Prior Publication Data

US 2005/0082204 A1 Apr. 21, 2005

Related U.S. Application Data

(63) Continuation-in-part of application No. 10/713,898, filed on Oct. 18, 2002, which is a continuation-in-part of application No. 09/962,802, filed on Sep. 24, 2001, now Pat. No. 6,610,256, which is a continuation of application No. 08/855,410, filed on May 13, 1997, now Pat. No. 6,294,136, which is a continuation of application No. 08/415,710, filed on Apr. 3, 1995, now Pat. No. 5,720,928.

(60) Provisional application No. 60/419,884, filed on Oct. 18, 2002.

(51) Int. Cl.
*B03B 13/00* (2006.01)
*C12Q 1/68* (2006.01)

(52) U.S. Cl. ............................................. 209/1; 435/6
(58) Field of Classification Search ........................ None
See application file for complete search history.

(56) References Cited

U.S. PATENT DOCUMENTS

| 4,473,452 A | 9/1984 | Cantor et al. |
| 4,695,548 A | 9/1987 | Cantor et al. |
| 4,737,251 A | 4/1988 | Carle et al. |
| 4,767,700 A | 8/1988 | Wallace |
| 4,870,004 A | 9/1989 | Conroy et al. |
| 5,059,294 A | 10/1991 | Lizardi |
| 5,079,169 A | 1/1992 | Chu et al. |
| 5,314,829 A | 5/1994 | Coles |
| 5,356,776 A * | 10/1994 | Kambara et al. ................ 435/6 |
| 5,380,833 A | 1/1995 | Urdea |
| 5,405,519 A | 4/1995 | Schwartz |
| 5,599,664 A | 2/1997 | Schwartz |
| 5,720,928 A | 2/1998 | Schwartz ..................... 422/186 |
| 5,985,549 A | 11/1999 | Singer et al. .................... 435/6 |
| 6,123,819 A | 9/2000 | Peeters |
| 6,147,198 A | 11/2000 | Schwartz |
| 6,150,089 A | 11/2000 | Schwartz |
| 6,265,153 B1 * | 7/2001 | Bensimon et al. .............. 435/6 |
| 6,294,136 B1 | 9/2001 | Schwartz ..................... 422/186 |
| 6,438,279 B1 | 8/2002 | Craighead et al. |
| 6,509,158 B1 * | 1/2003 | Schwartz ....................... 435/6 |
| 6,610,256 B2 | 8/2003 | Schwartz |
| 6,762,059 B2 * | 7/2004 | Chan et al. ................... 436/164 |
| 7,049,074 B2 * | 5/2006 | Schwartz ....................... 435/6 |
| 2002/0037499 A1 | 3/2002 | Quake et al. |
| 2002/0081744 A1 | 6/2002 | Chan et al. |
| 2002/0137218 A1 | 9/2002 | Mian et al. |
| 2003/0165964 A1 | 9/2003 | Hannah |
| 2005/0112606 A1 * | 5/2005 | Fuchs et al. .................... 435/6 |

FOREIGN PATENT DOCUMENTS

| FR | 2605472 | 4/1988 |
| WO | WO 84/02001 | 5/1984 |
| WO | WO 87/01955 | 9/1987 |
| WO | WO 94/18218 | 8/1994 |
| WO | WO 00/09757 | 2/2000 |

OTHER PUBLICATIONS

PCT Int'l Search Report.
Chih-Ming Ho, "Fluidics—The Link Between Micro and Nano Sciences and Technologies", Proceedings of the IEEE 14th Annual International Conference On Microelectro Mechancial Systems. MEMS 2001. Interlaken, Switzerland, Jan. 21-25, 2001, IEEE International Micro Electro Mechanical Systems Conference, New York, NY: IEEE, US, vol. Conf. 14, (Jan. 21, 2001), pp. 375-384, XP010534628 ISBN: 0-7803-5998-4, pp. 378-379.
Unger M A et al: "Monolithic Microfabricated Valves and Pumps by Multilayer Soft Lithography", Science, American Association For The Advancement Of Science, US, vol. 288, Apr. 7, 2000, pp. 113-116, XP002192277 ISSN: 0036-8075 Figure 1.
Stix, Gary; "Thinking Big-A Harvard Medical School dropout aims to usher in the personal-genomics ear," Innovations, Scientific American, Jun. 2002, pp. 30-31.
Stikeman, Alexandra, "Nanobiotech Makes The Diagnosis," Technology Review, May 2002, pp. 61-66.
Barlow and Lehrach, 1987, "Genetics by Gel Electrophoresis: The Impact of Pulsed Field Gel Electrophoresis on Mammalian Genetics", Trends on Genetics 3: 167-171.
Bensimon, et al., 1994, "Alignment and Sensitive Detection of DNA by a Moving Interface" Science 265: 2096-2098.
Burke et al., 1987, "Cloning of Large Segments of Exogenous DNA into Yeast by Means of Artificial Chromosome Vectors", Science 236: 806-812.

(Continued)

*Primary Examiner*—Gary Benzion
*Assistant Examiner*—Stephanie K Mummert
(74) *Attorney, Agent, or Firm*—Quarles & Brady LLP

(57) ABSTRACT

Laminar flow of a carrier liquid and polymeric molecules through micro-channels is used to straighten, align, separate, and/or sort the polymeric molecules. The polymeric molecules may be analyzed and/or manipulated in the carrier liquid or attached to a wall of the micro-channel for subsequent treatment and analysis. Micro-channels can be manufactured using an elastic molding material. One micro-channel embodiment provides fluid flow using a standard laboratory centrifuge.

67 Claims, 4 Drawing Sheets

OTHER PUBLICATIONS

Campbell et al., 1991, "Generation of a Nested Series of Interstitial Deletions in Yeast Artificial Chromosomes Carrying Human DNA", Proc. Natl. Acad. Sci. USA 88: 5744-5748.

Carle et al., 1986, "Electrophoretic Separations of Large DNA Molecules by Periodic Inversion of the Electric Field", Science 232: 65-68.

Cavalli-Sforza, 1990, "Opinion: How Can One Study Individual Variation for 3 Billion Nucleotides of the Human Genome", Am. J. Hum. Genet. 46: 649-651.

Chattoraj et al., 1978, "DNA Coordination with Polyamines", J. Mol. Biol. 121: 327-337.

Chumakov et al., 1992, "Continuum of Overlapping Clones Spanning the Entire Human Chromosome 21q", Nature 359: 380-387.

Church and Gilbert, 1984, "Genomic Sequencing", Proc. Natl. Acad. Sci. USA 81: 1991-1995.

Dev et al., 1982, "Techniques for Chromosome Analysis", Techniques in Somatic Cell Genetics, edited by Shay, pp. 493-503.

Ferrin and Camerini-Otero, 1991, "Selective Cleavage of Human DNA: RecA-Assisted Restriction Endonuclease (RARE) Cleavage", Science 254: 1494-1497.

Fish and Ziff, 1981, "A Sensitive Solid Phase Microradioimmunoassay for Anti-Double Stranded DNA Antibodies", Arthritis and Rheumatism 24: 534-543.

Gerlach et al., 1984, "Application of a High-Resolution TV-Microscope System to Estimate the Sequence of Centromere Separation in Muntjak Chromosomes", Cytometery 5: 562-571.

Glazer et al., 1997, "A Stable double-Stranded DNA-Ethidium Homodimer Complex: Application to Picogram Fluorescence Detection of DNA in Agarose Gels", Proc. Natl. Acad. Sci. USA 87: 3851-3855.

Gosule and Schellman, 1978, "DNA Condensation with Polyamines I. Spectroscopic Studies", J. Mol. Biol. 121: 311-326.

Guo et al., 1993, "Sizing of Large DNA Molecules by Hook Formation in a Loose Matrix", J. Biomol. Struct. and Dynam. 11: 1-10.

Guo et al., 1992, "Sizing Single DNA Molecules", Nature 359: 783-784.

Gurrieri et al., 1990, "Imaging of Kinked Configurations of DNA Molecules Undergoing Orthogonal Field Alternating Gel Electrophoresis by Fluorescence Microscopy", Biochemistry 2: 3396-3401.

Hansma et al., 1993, "Atomic Force Microscopy of DNA in Aqueous Solutions", Nucl. Acids Res. 21: 505-512.

Heng et al., 1992, "High-Resolution Mapping of Mammalian Genes by in situ Hybridization to Free Chromatin", Proc. Natl. Acad. Sci. USA 89: 9509-9513.

Houseal et al., "Real-Time Imaging of Single DNA Molecules with Fluorescence Microscopy", Biophys. J. 56: 507-516, 1989.

Karrasch et al., 1993, "Covalent Binding of Biological Samples to Solid Suports for Scanning Probe Microscopy in Buffer Solution", Biophysical J. 65: 2437-2446.

Khrapko et al., 1991, "A Method for DNA Sequencing by Hybridization with Oligonucleotide Matrix", J. DNA Sequencing and Mapping 1: 375-388.

Koob et al., 1992, "RecA-AC: Single-Site Cleavage of Plasmids and Chromosomes at Any Predetermined Restriction Site", Nucl. Acids Res. 20: 5831-5836.

Koob and Szybalski, 1990, "Cleaving Yeast and *Escherichia coli* Genomes at a Single Site", Science 250: 271-273.

Kucherlapati et al., 1988, Genetic Recombination pp. 92-106.

Lawrence et al., 1988, "Sensitive, High-Resolution Chromatin and Chromosome Mapping In Situ: Presence and Orientation of Two Closely Integrated Copies of EBV in a Lymphoma Line", Cell 52: 51-61.

Lichter et al., 1990, 1990, "High-Resolution Mapping of Human Chromosome 11 by in Situ Hybridization with Cosmid Clones", Science 247-64-69.

Link and Olson, 1991, "Physical Map of the *Saccharomyces cerevisiae* Genome at 110-Kilobase Resolution", Genetics 127: 681-698.

Lodish et al., 1995, Molecular Cell Biology, W.H. Freeman, NY, p. 345.

Luckham and Klein, 1984, "Forces Between Mica Surfaces Bearing Adsorbed Polyelectrolyte, Poly-L-lysine, in Aqueous Media", J. Chem. Soc. Faraday Trans. I, 80: 865-878.

Lyubchenko et al., 1992, "Atomic Force Microscopy Imaging of Double Stranded DNA and RNA", J. Biomol. Struct. and Dynam. 10: 589-606.

Maier et al., 1992, "Complete Coverage of the *Schizosaccharomyces pombe* Genome in Yeast Artificial Chromosomes", Nat. Genet. 1: 273-277.

Manuelidis et al., 1982, "High-Resolution Mapping of Satellite DNA Using Biotin-Labeled DNA Probes", J. Cell. Biol. 95: 619-625.

Massa, 1973, Flow Properties of High-Molecular-Weight DNA Solutions: Viscosity, Recoil, and Longest Retardatino Time, Biopolymrs 12:1071-1081.

Matsumoto et al., 1981, "Light Microscopic Structure of DNA in Solution Studied by the 4',6-Diamidino-2-phenylindole Staining Method", J. Mol. Biol. 152:501-516.

Murray and Szostak, 1983, "Construction of Artificial Chromosomes in Yeast", Nature 305;189-193.

Ohi et al., 1978, "Mapping of Mitochondria 4S RNA Genes in *Xenopus laevis* by Electron Microscopy", J. Mol. Biol. 121:299-310.

Perkins et al., 1994, "Direct Observation of Tube-like Motion of a Single Polymer Chain", Science 264:819-822.

Porath and Axen, 1976, Immobilization of Enzymes to Agar, Agarose, and Sehadex Supports:, Meth. Enzymol. 44:19-45.

Rampino and Chrambach, 1991, "Conformational Correlatives of DNA Band Compression and Bidirectional Migration During Field Inversion Gel Electrophoresis, Detected by Quantitative Video Epifluorescence Microscopy", Biopolymers 31:1297-1307.

Romling et al., 1989, "A Physical Genome Map of *Pseudomonas aeruginosa*", EMBO J. 8:4081-4089.

Schwartz et al., 1989, "Conformational Dynamics of Indivdival DNA Molecules During Gel Electrophoresis", Nature 338-520-522.

Schwartz et al., 1989, "ED: Pulsed Electrophoresis Instrument", Nature 342-575-576.

Schwartz and Cantor, 1984, "Separations of Yeast Chromosome-Sized DNAs by Pulsed Field Gradient Gel Electrophoresis", Cell 37:67-75.

Smith et al., 1992, "Direct Mechanical Measurements of the Elasticity of Single DNA Molecules by Using Magnetic Beads", Science 258:1122-1126.

Smith and Bendich, 1990, "Electrophoretic Charge Density and Persistence Length of DNA as Measured by Fluorecence Microscopy", Biopolymers 29:1167-1173.

Smith et al., 1989, "Observation of Individual DNA Molecules Undergoing el Electrophoresis", Science 242:203-206.

Smith and Bimstiel, 1976, "A Simple Method for DNA Restriction Site Mapping", Nucl. Acids Res. 3:2387-2399.

Southern, 1975, "Detection of Specific Sequences among DNA Fragments Separated by Gel Electrophoresis", J. Mol. Biol. 98:503-517.

Stallings et al., 1990, "Physical Mapping of Human Chromosomes by Repetitive Sequence Fingerprinting", Proc. Natl. Acad. Sci. USA 87:6218-6222.

Stellwagen, 1988, "Effect of Pulsed and Reversing Electric Fields on the Orientation of Linear and Supercoiled DNA Molecules in Agarose Gels", Biochemistry 27:6417-6424.

Stellwagen, N.C., 1985, "Orientation of DNA Molecules in Agarose Gels by Pulsed Electric Fields", J. Biomo. Str. and Dynam. 3:299-314.

Sturn and Weill, 1989, Direct Observation of DNA Chain Orientation and Relaxation by Electric Birefrigence: Implications for the Mechanism of Separation During Pulsed-Field Gel Electrophoresis:, Physical Rev. Letters 62:1484-1487.

van den Engh et al., 1992, "Estimating Genomic Distance from DNA Sequence Location in Cell Nuclei by a Random Walk Model", Science 257:1410-1412.

Williams, 1977, Use of Polylisine for Adsorbtion of Nucleic Acids and Enzymes to Electron Microscope Specimen Films:, Proc. Natl. Acad. Sci. USA 74:2311-2315.

Woolf et al., 1988, "Mapping Genomic Organization by Field Inversion and Two Dimensional Gel Electrophoresis", Nucl. Acids. Res. 16:3863-3875.

Yanagida et al., 1983, "Dynamic Behaviors of DNA Molecules in Solution . . . " Cold Spring Harbor Symp. Quant. Biol. 47:177-187.

Zenhausern et al., 1992, "Imaging of DNA by Scanning Force Microscopy", J. Struct. Biol. 108:69-73.

Zubay, 1988, Biochemistry (Macmillan Publishing Company, New York) pp. 918-919.

Houseal et al., 1989, "Real-Time Imaging of Single DNA Molecules with Fluorescence Microscopy", Biophys. J. 56: 507-516.

Chattoraj et al., "DNA Condensation with Polyamines", J. Mol. Biol. 121, (1978), pp. 327-337.

Ohi et al., "Mapping of Mitochondrial 4S RNA Genes . . . by Electron Microscopy", J. Mol. Biol. 212, (1978), pp. 299-310.

Manuelidis et al, Biol. Abstr. 76(4); Ref. No. 27153; p. 2940.

Bensimon, A. et al., 1994, "Alignment and Sensitive Detection of DNA by a Moving Interface" Science 265: 2096.

Perkins, T.T. et al., 1994, "Direct Observation of Tube-like Motion of a Single Polymer Chain", 264: 819-822.

Guo et al., 1993, "Sizing of Large DNA Molecules by Hook Formation in a Loose Matrix", J. Biomol. Structure and Dynamics 11: 1-10.

Hansma, H.G. et al., 1993, "Atomic force microscopy of DNA in aqueous solutions", Nucleic Acids Research 21: 505-512.

Karrasch, S. et al., 1993, "Covalent Binding of Biological Samples to Solid Supports for Scanning Probe Microscopy in Buffer Solution" Biophysical J. 65: 2437-2446.

Koob et al., 1992, "RecA-AC: single-site cleavage of plasmids and chromosomes at any predetermined restriction site" Nucleic Acids Res. 20:5831.

Lyubchenko et al., 1992, "Atomic Force Microscopy Imaging of Dougle Stranded DNA and RNA", J. Biomol. Struct. and Dyn. 10: 589-606.

van denEngh, et al., 1992, "Estimating Genomic Distance from DNA Sequence Location in Cell Nuclei by a Random Walk Model", Science 257: 1410.

Heng et al., 1992, "High-resolution mapping of mammalian genes by in situ hybridization to free chromatin", Proc. Natl. Acad. Sci. USA 89: 9509.

Maier et al., 1992, "Complete coverage of the *Schizosaccharomyces pombe* genome in yeast artificial chromosomes", Nat. Genet. 1:273.

Guo et al., 1992, "Sizing single DNA molecules", Nature 359:783-784.

Chumakov et al., 1992, "Continuum of overlapping clones spanning the entire human chromosome 21q", Nature 359:380.

Link, 1991, "Physical Map of the *Saccharomyces cerevisiae* Genome at 110-Kilobase Resolution", Genetics 127: 681.

Ferrin et al., 1991, "Selective Cleavage of Human DNA: RecA-Assisted Restriction Endonuclease (RARE) Cleavage", Science 254: 1494.

Campbell et al., 1991, "Generation of a nested series of interstitial deletions in yeast artificial chromosomes carrying human DNA", Proc. Natl. Acad. Sci. USA 88:5744.

Cavalli-Sforza, 1990, "Opinion: How Can One Study Individual Variation for 3 Billion Nucleotides of the Human Genome", Am. J. Hum. Genet. 46: 649.

Koob et al., 1990, "Cleaving Yeast and *Escherichia coli* Genomes at a single site", Science 250: 271-273.

Lichter et al., 1990, "High-Resolution Mapping of Human Chromosome 11 by in Situ Hybridization with Cosmid Clones" Science 247: 64.

Glazer et al., 1990, "A stable double-stranded DNA-ethidium homodimer complex: Application to picogram fluorescence detection of DNA in agarose gels", Proc. Natl. Acad. Sci. USA 87: 3851.

Lawrence et al., 1988, "Sensitive, High-Resolution Chromatin and Chromosome Mapping In Situ: Presence and Orientation of Two Closely Integrated Copies of EBV in a Lymphoma Line", Cell 52:51.

Barlow et al., 1987, Genetics by gel electrophoresis: the impact of pulsed field gel electrophoresis on mammalian genetics:, Trends in Genetics 3: 167-177.

Burke et al., 1987, "Cloning of Large Segments of Exogenous DNA into Yeast by Means of Artificial Chromosome Vectors", Science 236: 806.

Church and Gilbert, 1984, "Genomic sequencing", Proc. Natl. Acad. Sci. USA 81: 1991.

Luckham and Klein, 1984, "Forces between Mica Surfaces Bearing adsorbed Polyelectrolyte, Poly-L-lysine, in Aqueous Media", Chem. Soc. Faraday Trans. I, 80: 865-878.

Schwartz and Cantor, 1984, "Separation of Yeast Chromosome-Sized DNAs by Pulsed Field Gradient Gel Electrophoresis", Cell 37: 67.

Murray and Szostak, 1983, "Construction of Artificial Chromosome in Yeast", Nature 305: 189-193.

Manuelidis et al., 1982, "High-resolution Mapping of Satellite DNA using Biotin-labeled DNA Probes", J. Cell Biol. 95: 619.

Matsumoto, et al., 1981, "Light Microscopic Structure of DNA in Solution Studied by the 4',6-Diamidino-2-phenylindole Staining Method", J. Mol. Biol. 132: 501-516.

Gosule and Schellman, 1978, "DNA Condensation with Polyamines", J. Mol. Biol. 121: 311-326.

Porath and Axen, 1976, "Immobilization of Enzymes to Agar, Agarose, and Sephadex Support", Methods Enzymol. 44:19.

Smith and Bimstiel, 1976, "A simple method for DNA restriction site mapping", Nucleic Acids Res. 3: 2387-2399.

Massa et al., 1973, "Flow Properties of High-Molecular-Weight DNA Solutions: Viscosity, Recoil, and:Longest Retardation Time", Biopolymers 12:.

Schwartz et al., 1989, "Conformational Dynamics of Individual DNA Molecules During Gel Electrophoresis", Nature 338:520.

Rampino and Chrambach, 1991, "Conformational correlatives of DNA band compression and bidirectional migration during field inversion gel electrophoresis, detected by quantitative video epifluoresence microscopy", Biopolymers 31: 1297-1307.

Romling et al., 1989, "A physical genome map of *Pseudomonas aeruginosa* ", EMBO J. 8(13): 4081-4089.

Smith et al., 1989, "Observation of Individual DNA Molecules Undergoing Gel Electrophoresis", Science 242: 203.

Woolf et al., 1988, "Mapping genomic organizatiaon by field inversion and two dimensional gel electrophoresis", Nucleic Acids Research 16(9): 3863.

Carle et al., Electrophoretic Separations of Large DNA Molecules by Periodic Inversion of the Electrif Field, Science 232: 65-68.

Stellwagen, N.C., 1985, "Orientation of DNA molecules in agarose gels by pulsed electric fields", J. Biomol. Str. and Dyn. 3(2): 299.

Yanagida et al., 1983, "Dynamic behaviors of DNA Molecules in solution . . . " Cold Spring Harbor Symp. Quant. Biol. 47: 177.

Dev. et al., 1982, "Techniques for chromosome analysis", Techniques in Somatic Cell Genetics, edited by Shay, pp. 493-503.

Manuelidis et al., 1992, "High-resolution mapping of satellite DNA using biotin-labeled DNA probes", Biol. Abstr. 76(4), Ref. No. 27153, p. 2940.

Chattoraj et al., 1978, "DNA Coordination with polyamines", J. Mol. Biol. 121: 327.

Ohi et al., 1978, "Mapping of Mitochondria 4S RNA genes in *Xenopus laevis* by electron microscopy", J. Mol. Biol. 121: 299.

Gurrieri et al., 1990, "Imaging of kinked configurations of DNA molecules undergoing orthogonal field alternating gel electrophoresis by fluorescence microscopy", Biochemistry 29: 3396-3401.

Smith and Bendich, 1990, "Electrophoretic charge density and persistance length of DNA as measured by fluorescence microscopy", Biopolymers 29(8-9): 1167.

Sturm and Weill, 1989, "Direct observation of DNA chain orientation and relaxation by electric birefringence: Implications for the mechanism of separation during pulsed-field gel electrophoresis", Physical Rev. Letters 62(13): 1484.

Stellwagen, 1988, "Effect of pulsed and reversing electric fields on the orientation of linear and supercoiled DNA molecules in Agarose Gels", Biochemistry 27: 6417.

Schwartz, et al., "Conformational Dynamics of Individual DNA Molecules During Gel Electrophoesis", Nature, Apr. 6, 1989, pp. 520-522.

Poddar et al., Chromosome analysis by two-dimensional fingerprinting, Gene, 49 (1986), pp. 93-102.

Woolf et al., "Mapping genomic organization by field inversion and two dimensional gel electrophoresis", Nucleic Acid Research, vol. 16, No. 9 (1988), pp. 3863-3875.

Roemling et al., "A physical genome map of *Pseudomonas aeruginosa*", The EMBO Journal, vol. 8, No. 13 (1989), pp. 4081-4089.

Yanagida et al., "Dynamic Behaviors of DNA Molecules in Solution . . . ", Cold Sprg. Hrbr. Symp. Quant. Biol. 47, pp. 177-187, 1983.

Zubay, Biochemistry, 1988, pp. 918-919.

Kucherlapati et al., Genetic Recombination, 1988, pp. 92-106.

Smith et al., "Observation of Individual DNA Molecules Undergoing Gel Electrophoresis", Science 242, Jan. 13, 1989 pp. 203-206.

Carle et al., "Electrophoretic Separations of Large DNA molecules . . . ", Science, Apr. 4, 1986, pp. 65-68.

Dev. et al., "Techniques for Chromosome Analysis", Techniques in SOmatic Cell Genetics, edited by Shay, 1982, pp. 493-503.

Rampino, "The Physics of Gel Electrophoresis", 1989.

Stellwagon, "Effect of Pulsed and Reversing Electric Fields . . . " Biochem. 17, 1988, pp. 6417-6424.

Manuelidis et al., Biol. Abstr. 76(4), Ref. No. 27153, p. 2940, 1992.

Gerlach et al. (1984) Cytometry 5:562-571.

K. R. Khrapko et al., "A Method for DNA Sequencing by Hybridization With Oligonucleotide Matrix", J. DNA Sequencing and Mapping, 1991, vol. 1, pp. 375-388.

R. C.Williams, "Use Of POlylysine for Adsorption Of Nucleic Acids and Enzymes To Electron Microscope Specimen Films", Proc. Natl. Acad. Sci. USA, vol. 74, No. 6, pp. 2311-2315, Jun. 1977.

F. Fish et al., "A sensitive Solid Phase Microradioimmunoassay For Anti-Dougle Stranded DNA Antibodies", Arthritis and Rheumatism, vol. 24, No. 3 (Mar. 1981).

\* cited by examiner

MICRO-CHANNEL LONG MOLECULE MANIPULATION SYSTEM

CROSS-REFERENCE TO RELATED APPLICATIONS

This application is a continuation in part of U.S. application Ser. No. 10/713,898 being a conversion of U.S. Provisional application 60/419,884 filed Oct. 18, 2002, hereby incorporated by reference, which is a continuation in part of application Ser. No. 09/962,802 now U.S. Pat. No. 6,610,256 filed Sep. 24, 2001, which is a continuation of application Ser. No. 08/855,410 now U.S. Pat. No. 6,294,136, filed May 13, 1997, which is a continuation of application Ser. No. 08/415,710 now U.S. Pat. No. 5,720,928, filed Apr. 3, 1995, all hereby incorporated by reference.

Alternatively, this application claims the benefit of U.S. Provisional application 60/419,884 filed Oct. 18, 2002, hereby incorporated by reference.

STATEMENT REGARDING FEDERALLY SPONSORED RESEARCH OR DEVELOPMENT

This invention was made with United States government support awarded by the following agencies: DOE DE-FGO2-99ER62830 and NIH HG00225.

The United States has certain rights in this invention.

BACKGROUND OF THE INVENTION

The present invention relates to methods of manipulating molecules and, in particular, to a fluid transport system useful for straightening, aligning, and fixing long chain polymers such as DNA.

The analysis of nucleic acid molecules (e.g. DNA) and, in particular, the sequencing of such molecules, may be aided by optical techniques in which long portions of such molecules are straightened and fixed to a substrate for microscopic analysis. The fixed molecule may be analyzed by creating "landmarks" on the molecule by attaching fluorescent markers to specific locations or by cutting it with restriction enzymes to form visible breaks at specific locations. The order and relative separation of the landmarks is preserved because the molecule remains fixed, and may be used to produce an optical map of the molecule. The optical map provides a framework on which other sequence information may be assembled. The landmarks allow optical maps of fragments of long molecules to be assembled into the entire molecule by the process of matching fragments with similarly spaced landmarks.

The effective use of optical maps requires that large numbers of single molecules be processed. A number of techniques have been examined for the purpose of straightening and fixing large numbers of molecules including: (1) straightening the molecules in a flow of molten gel which is then hardened to fix the molecules in place, and (2) straightening the molecules under capillary flow of a carrier liquid or convective flow caused by evaporation of a carrier liquid and promoting adsorption of the elongated molecules to a substrate adjacent to the flow.

Ideally, when molecules are fixed to a substrate for optical analyses, the fixed molecules should be straightened with uniform elongation, aligned to be substantially parallel, and have sufficient separation so that molecules do not overlap or cross. Points of overlap create image artifacts that can severely hamper the analysis process. Optionally it may be desired that the straightened molecules be separated from small fragments and be of comparable size.

It is typical to stain the fixed molecule with a fluorescent material which distributes itself evenly along the molecule allowing estimates of separation between landmarks (e.g., in numbers of base pairs) to be gauged by total fluorescence rather than strictly by length. Such fluorescence measurements work best if the elongation of the molecule during straightening is not so great as to decrease the fluorescence per length of the molecule to a background level. Inadequate elongation of the molecule, however, can make it difficult to identify the points cut by the restriction enzymes which desirably separate slightly under relaxation of the elongated molecule to render the cuts visible.

Prior art techniques for elongating and fixing long chain molecules can produce excessive overlap among molecules and variation in molecule elongation.

SUMMARY OF THE INVENTION

The present invention provides a method for straightening, aligning, separating, and/or sorting polymeric molecules using well-controlled laminar flow in a micro-channel. The molecules may be fixed to a substrate after straightening, aligning, separating and/or sorting, or may be analyzed suspended in a carrier liquid during continuous flow or using a hovering technique in which laminar flow is periodically reversed. The present invention also provides an improved method of fabricating micro-channels and a simple mechanism for producing the necessary laminar flow.

Specifically then, one aspect of the present invention provides a method for elongating, separating, and/or aligning polymeric molecules comprising the steps of passing a liquid and polymeric molecule through a micro-channel sized to provide laminar flow of the liquid along a micro-channel length. The flow of liquid is controlled to cause elongation of the polymeric molecule within the laminar flow without significant shearing.

It is thus one object of the invention to provide a method for straightening polymeric molecules that normally assume a coiled configuration. The straightening is performed without mechanical "carding" in which microscopic posts either machined in silicon or formed of the microscopic structure of a gel or the like. These latter techniques do not produce uniformly elongated molecules and are often difficult to fabricate and can easily foul and obstruct further manipulation or observation of the molecule.

The elongated molecule may be viewed through a transparent wall of the micro-channel as supported in the carrier liquid, and/or may be manipulated through the introduction of a reactant such as an enzyme or other molecule possibly with stimulation by radiation, for example, with a focused laser.

Thus, it is another object of the invention to provide a method of elongating polymeric molecules that allows concurrent viewing and/or manipulation of the molecules in the elongated state.

The laminar flow may be periodically reversed to cause the polymeric molecule to hover in the elongated state.

Thus, it is another object of the invention to provide for indefinite elongation of molecules in a localized region such as may assist in manipulation or analysis of that elongated molecule.

One wall of the micro-channel may provide electrostatic attraction to the polymeric molecule, and the method may include the step of adsorbing the polymeric molecule to the first wall of the micro-channel in the elongated form.

Thus, it is another object of the invention to allow fixation of the molecule for further analysis, manipulation, and/or storage.

The fixation may be affected by random encounters between the ends of the polymeric molecule and a wall of the micro-channel or by an external force such as an applied electrostatic or centrifugal acceleration.

Thus, it is another object of the invention to provide a variety of different methods of fixing the polymeric molecule to a substrate such as may also provide selectivity in the fixation or other advantages.

Another aspect of the invention is that it may provide for a separating of polymeric molecules of differing molecular weights by controlling the laminar flow of the liquid holding the polymeric molecules. This sorting may make use of the varying speeds in the laminar flow of elongated molecules as a function of their length and/or weight, or a functional dependence between the unfolding of the molecules and flow velocity and/or differences in diffusion rate of the ends of the molecule as a function of molecular length.

Thus, it is another object of the invention to provide a method of sorting molecules using laminar flow within a channel.

When the laminar flow is used to distinguish molecules on the basis of whether they are folded and unfolded, molecules may be separated by the laminar flow acting on their different configurations, or by adsorbing the unfolded molecules to a substrate, or by optical systems that may be distinguished between folded and unfolded molecules.

In one embodiment, the apparatus used in the present invention may include an optical mapping surface and an elastic channel material releasably adhered to the optical mapping surface to create the micro-channel between the elastic channel material and the optical mapping surface sized to provide flow of a liquid and the polymeric molecule along a micro-channel length.

Thus, it is another object of the invention to provide a simple method of fabricating micro-channels for use in this application. Since the micro-channel can be removed from the optical mapping surface, when molecules are mounted on the surface they may be analyzed with any type of microscope, including electron microscopes, and are not limited to analyses with light microscopes that might penetrate a transparent optical mapping surface.

The first wall of the micro-channel may be transparent, for example, glass.

Thus, it is another object of the invention to provide a surface that may be used with an optical microscope to view molecules held in a carrier liquid in the micro-channel or adhered to the surface viewed through the surface.

At least one end of the micro-channel may provide a funnel section opening to a reservoir holding the liquid and polymeric molecules.

It is thus another object of the invention to provide a system that may accommodate molecules held in a liquid carrier and multiple molecules for high through-put.

The reservoir may be at least one end well extending perpendicular to the length of the micro-channel and wherein the apparatus further includes a housing allowing the end well and micro-channel to be received by a centrifuge with the end well extending along a principal axis of centrifugal acceleration and the micro-channel extending substantially across the principal axis of centrifugal acceleration.

Thus, it is another object of the invention to provide a simple apparatus that makes use of a standard laboratory centrifuge to produce the necessary flows and which thus may be inexpensive and/or disposable.

The micro-channel may include a region of varying cross section to promote a gradient in flow rate.

Thus, it is another object of the invention to provide for a sorting of molecules by length, taking advantage of different flow rates affecting adhesion of the molecules of different lengths.

These particular objects and advantages may apply to only some embodiments falling within the claims and thus do not define the scope of the invention.

DETAILED DESCRIPTION OF THE PREFERRED EMBODIMENT

Figure 1:
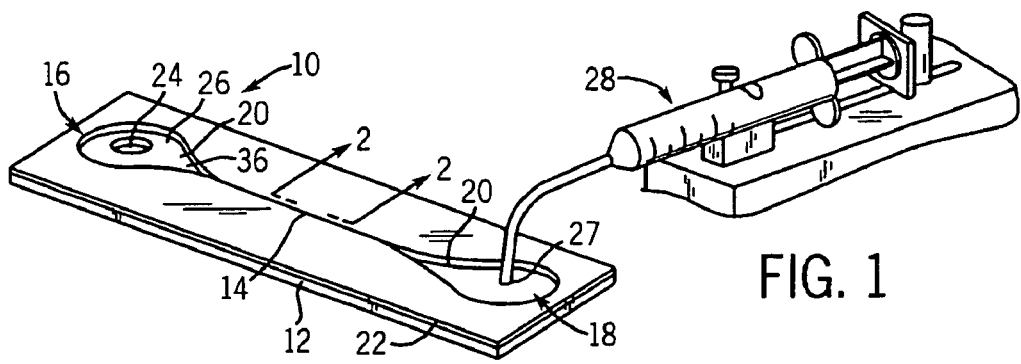
FIG. 1 is a perspective view of one embodiment of the present invention showing a micro-channel communicating between a staging reservoir, holding polymeric molecules in a carrier liquid, and a collecting reservoir; the micro-channel attached to the reservoirs by funnel portions reducing shear and promoting laminar flow in the micro-channel and showing the use of a syringe pump to draw liquid through the micro-channel.

Referring now to FIG. 1, the apparatus 10 of the present invention provides a generally planar channel plate 12 into which a longitudinally extending micro-channel 14 is formed, flanked by a staging reservoir 16 and a collecting reservoir 18 positioned at longitudinal ends of the channel plate 12.

Junctions between the longitudinal ends of the micro-channel 14 and staging reservoir 16 and collecting reservoir 18 are tapered to create funnel sections with narrow ends attached to the micro-channel 14 and wide ends attached to one of the staging reservoir 16 or collecting reservoir 18. The funnel sections 20 provide a smooth transition of fluid from the staging reservoir 16 through the micro-channel 14 to the collecting reservoir 18 thereby promoting laminar flow within the micro-channel 14 and reducing breakage of polymeric molecules as will be described.

One common wall of the staging reservoir 16, the collecting reservoir 18, and the micro-channel 14 is provided by an optical mapping substrate 22 attached to the channel plate 12. The substrate 22 thus encloses the staging reservoir 16, the collecting reservoir 18, and the micro-channel 14. The substrate 22, for example, may be a glass slide, treated, as will be described below.

In the embodiment of FIG. 1, a sample introduction port 24 may be formed in the optical mapping substrate 22 at the staging reservoir 16 to allow the introduction of polymeric molecules 36 and a carrier liquid 26 to the staging reservoir. In particular embodiments, the sample introduction port 24 may be used for pressure equalization when materials are drawn through the micro-channel 14 or for the attachment of a pump to pressurize the staging reservoir 16 to cause materials to flow through the micro-channel 14.

Similarly, a sample extraction port 27 may be formed in the optical mapping substrate 22 at the collecting reservoir 18 for removal of material, pressure equalization, or as shown, the attachment of pump 28 to draw the materials through the micro-channel 14. Alternatively, the ports 24 and 27 may be formed in the channel plate 12.

In the embodiment of FIG. 1, the pump 28 is a syringe pump providing precisely metered flow using an electromechanical actuator and control system as is well understood in the art. The syringe pump draws carrier liquid 26 and polymeric molecules 36 from staging reservoir 16 through the micro-channel 14 in the collecting reservoir 18 at a controlled flow rate as may be set to provide the desired laminar flow within the micro-channel 14.

Figure 2:
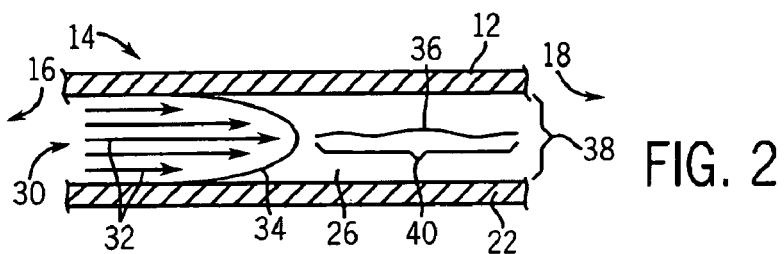
FIG. 2 is a cross-sectional view of the channel along lines 2-2 of FIG. 1 showing the increasing velocity of the laminar flow in the micro-channel toward the center of the micro-channel and an elongated DNA molecule centered in the micro-channel by the laminar flow.

Specifically, referring to FIG. 2, the laminar flow 30 of carrier liquid 26 and polymeric molecules 36 within the micro-channel is such as to provide flow 32 parallel to the longitudinal walls of the micro-channel 14 with greatest flow velocities toward the cross-sectional center of the micro-channel 14 thereby defining a flow velocity profile 34. The flow rate of the pump 28 and the size of the micro-channel 14 is selected to provide flow velocity profile 34 that promotes straightening of the particular polymeric molecule 36 contained within the carrier liquid 26 with the polymeric molecule 36 roughly centered within the lumen of the micro-channel 14. These settings may be determined empirically by visual observation of the polymeric molecules 36 at different flow rates. Generally, laminar flow may be distinguished from capillary flow in which the liquid is drawn along the surface of the micro-channel 14 walls by the hydrophilic nature of those walls and where the center leading flow velocity profile 34 is not obtained.

In a 50-micrometer wide micro-channel 14, for example, the velocity of flow 32 may range from 15 to 70 micrometers per second as measured across the lumen of the micro-channel 14. Alternatively, in a channel having a 100×20 micron opening, one acceptable flow would be approximately $5 \times 10^{-2}$ nl/sec.

In one embodiment, the cross-sectional width 38 of the micro-channel 14 is 50 micrometers and is preferably less than 100 micrometers. More generally, it is believed that the width 38 will be between one and one hundred times the straightened length 40 of the polymeric molecule 36.

Figure 3:
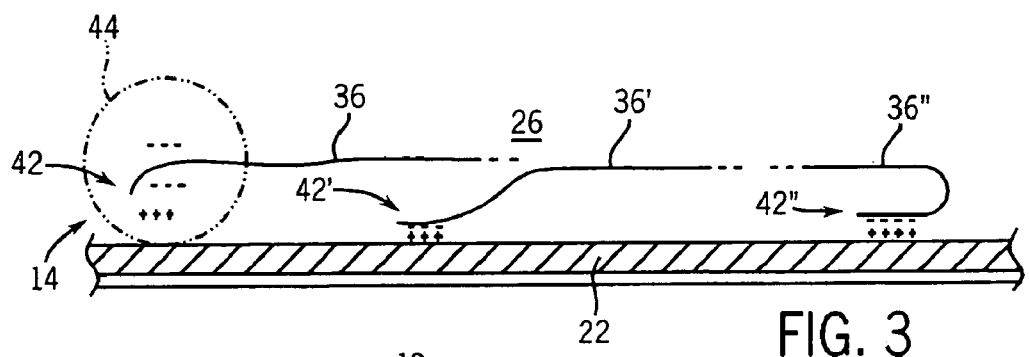
FIG. 3 is a fragmentary view similar to FIG. 2 showing: a diffusion radius of one end of a polymeric molecule prior to adsorption to a wall of the micro-channel; a polymeric molecule having a trailing end attached to the wall of the micro-channel; and a polymeric molecule having a leading end attached to the wall of the micro-channel prior to adsorption of the entire length of the polymeric molecule to the wall of the micro-channel.

Referring now to FIG. 3, although the inventors do not wish to be bound by a particular theory, it is believed that the ends 42 of the polymeric molecule 36 are more mobile than the remainder of the polymeric molecule 36 and may be modeled as having an effective diffusion radius 44 during the time the polymeric molecule 36 is in transit in the micro-channel 14 and generally greater than the polymeric molecule 36 as a whole. The average flow rate of the carrier liquid 26 for the flow velocity profile 34 and the width 38 of the micro-channel 14 is thus adjusted so that this effective diffusion radius 44 is equal to or greater than the width 38 of the micro-channel 14. In this way, at some time during transit of the polymeric molecule 36 within the micro-channel 14, contact by one end 42 of a large number of the polymeric molecules 36 with the substrate 22 can be expected. This contact will cause an electrostatic bond between the substrate 22 and the end 42 of a polymeric molecule 36.

Either the leading or the trailing ends 42 of the polymeric molecule 36 may be the first to attach to the substrate 22. As indicated by polymeric molecule 36', if the trailing end 42' of the polymeric molecule 36" is the first to contact the substrate 22, it is believed that continued flow of the carrier liquid 26 pulls the remainder of the polymeric molecule 36 against the substrate 22 to be held there by electrostatic attraction in a straightened state. Conversely, as indicated by polymeric molecule 36", if the leading end 42" of the polymeric molecule 36" is the first to contact the substrate 22, it is believed that continued flow of the carrier liquid 26 rolls the remainder of the polymeric molecule 36 over and then draws it against the substrate 22 to be held there by electrostatic attraction in a straightened state.

In order to promote and control attachment of the polymeric molecule to the substrate 22, the substrate 22 may be treated to establish a positive charge density on its surface contacting the carrier liquid 26. For example, the surface may be a derivative with silage compounds, for example, those discussed in U.S. Pat. No. 5,720,928, hereby incorporated in its entirety by reference.

Whereas the micro-channels 14 and optionally the staging reservoir 16, and collecting reservoir 18 of the apparatus 10 may be constructed in silicon using conventional photolithographic techniques. In a preferred embodiment of the present invention, the micro-channels 14 (and optionally the staging reservoir 16 and collecting reservoir 18) are constructed using a molded elastomeric polymer.

Figure 4:
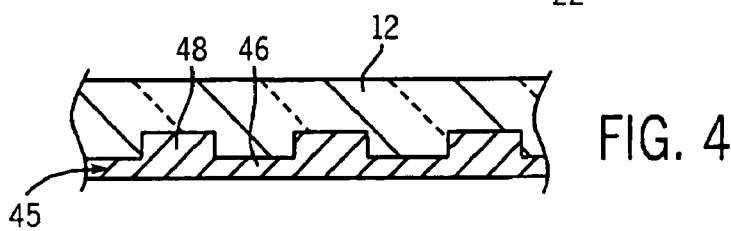
FIG. 4 is a cross-sectional view of multiple micro-channels during a first step of manufacturing the micro-channels in which a mold is used with an elastic molding compound to form upper walls of the micro-channels.

Referring now to FIG. 4 in particular, a mold 45 providing a planar substrate 46 with upstanding ridges 48 defining the volume of the micro-channels 14 may be fabricated using conventional photolithography in which a light sensitive photoresist is applied to a silicon wafer that will form the mold 45. The photoresist is hardened by selective optical exposure and the unhardened portions washed away so that the photoresist provides a mask in the regions of the upstanding ridges 48 (e.g., the regions of the micro-channels 14 and the staging reservoir 16 and collecting reservoir 18). The silicon wafer is then etched to a depth of 7 to 8 micrometers defining the height of the micro-channel 14.

Referring still to FIG. 4, an elastomeric polymer, preferably poly(dimethylsiloxane) ("PDMS") is then poured over this mold 45 to create the channel plate 12. The PDMS channel plate 12 is then peeled from the mold 45 and exposed to oxygen plasma to make it hydrophilic.

Figure 5:
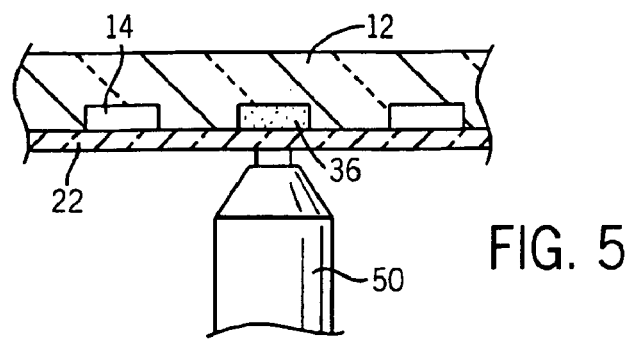
FIG. 5 is a figure similar to FIG. 4 showing removal of the mold and attachment of the upper walls of the micro-channel to a glass optical mapping surface in a second step of manufacturing.

As shown in FIG. 5, the channel plate 12 may then be adhered to the substrate 22 creating the micro-channels 14 and optionally the staging reservoir 16 and collecting reservoir 18. The PDMS of the channel plate 12 will naturally adhere to glass in a releasable manner to produce a leak resistant seal. The seal is strong enough to resist leakage of fluids filling the micro-channels for the pressures used in this process, yet weak enough to be reversible, and thus make the channel plate 12 and substrates 22 reusable.

By treatment of the substrate 22, as described above, to impress upon it a positive charge, and lack of treatment of channel plate 12 or by a treatment that promotes a negative surface charge on the channel plate 12 preferential adsorption of the polymeric molecules 36 by the substrate 22 may be promoted. Optical mapping of the fixed polymeric molecules 36 may then be done through the transparent glass substrate 22 by means of an inverted microscope objective 50 such as a Zeiss Axiovert 135M such as is readily commercially available. Before the optical mapping, the polymeric molecule may be treated with fluorescent markers or restriction enzymes as are understood in the art.

Alternatively, because the channel plate 12 is attached to the substrate 22 and releasable, the substrate 22 may be removed from the channel plate 12 and the top surface of the substrate 22 may be imaged. The removal of the channel plate 12 may also assist in further treatment of the fixed polymeric molecules 36, for example, with restriction enzymes and the like and the drying of these molecules to further promote adhesion. The ability to separate the channel plate 12 and substrate 22 allows one or both of these elements to be reused if desired.

Figure 6:
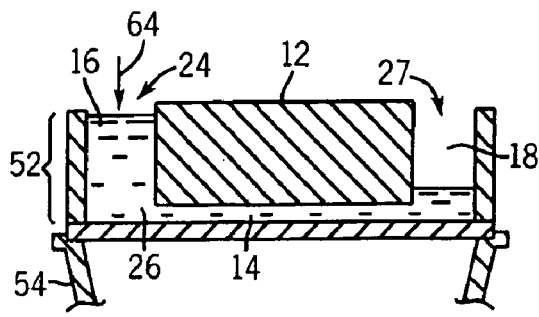
FIG. 6 is an elevational, cross-sectional view of an alternative embodiment of the present invention in which centrifugal acceleration acting on a fluid head in the staging reservoir causes laminar flow in the micro-channel.

Referring now to FIG. 6, in an alternative embodiment to that shown in FIG. 1, the height of the staging reservoir 16 and a collecting reservoir 18 may be increased and ports 24 and 27 provided through the channel plate 12 opposite the substrate 22. Upon initially filling staging reservoir 16 with carrier liquid 26 and polymeric molecules 36, a pressure head 52 is created being the difference in liquid height in staging reservoir 16 and a collecting reservoir 18. The small size of the micro-channel 14 limits flow from the staging reservoir 16 to the collecting reservoir 18 under normal gravitational acceleration after limited capillary flow.

Figure 8:
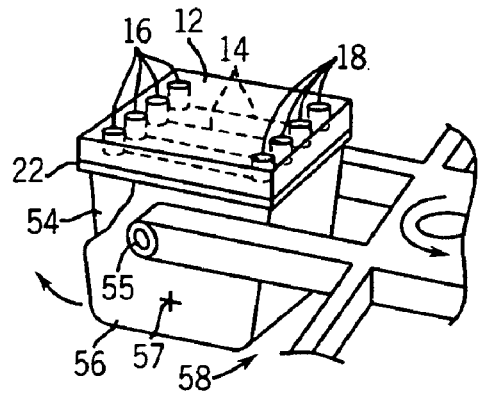
FIG. 8 is a perspective view of the embodiments of FIGS. 6 and 7 as placed in a standard centrifuge cup, the latter in partial cut-away.

Referring now to FIG. 8, the substrate 22 of the embodiment of FIG. 6 may be attached to a weighted carrier 54 that fits within the cup 56 of a standard swing bucket centrifuge 58 with the channel plate 12 supported to be level with the top of the cup 56 and the staging reservoir 16 and collecting reservoir 18 extending upward therefrom. The weighted carrier 54 is constructed so that the combination of the channel plate 12, the substrate 22, and the weighted carrier 54, when in position in the cup 56, have a center of mass 57 below the pivot 55 about which the cup is free to rotate.

Figure 9:
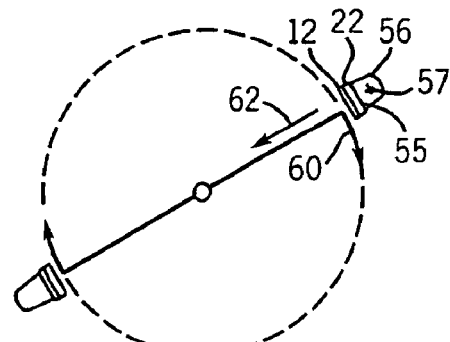
FIG. 9 is a simplified diagram of rotation of the centrifuge cup of FIG. 8 showing the vectors of motion and centripetal acceleration.

When the centrifuge is started, as shown in FIG. 9, rotation 60 of the cups 56 swings them outward under the influence of a radial centripetal acceleration 62 acting on the center of mass 57. The acceleration promotes a downward force 64 shown in FIG. 6 on the carrier liquid 26 sufficient to cause the desired laminar flow through the micro-channel 14. By sizing the aperture of the micro-channel 14, and controlling the initial pressure head 52, the desired flow rate may be achieved.

Figure 7:
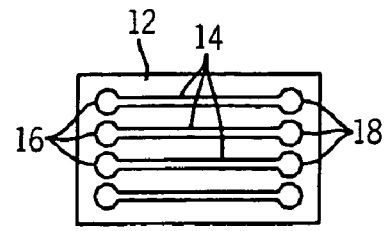
FIG. 7 is a plan view of the embodiment of FIG. 6 showing multiple parallel micro-channels, each with staging wells and receiving wells.

Referring to FIGS. 6 and 7, a single channel plate 12 may incorporate multiple staging reservoirs 16, collecting reservoirs 18, and intervening micro-channels 14. As the pressure head 52 drops with flow through the micro-channel 14, the flow rate through the micro-channel 14 will also decrease. Control of this rate of decrease can be obtained by adjusting the relative diameter or cross-sectional area of staging reservoir 16 compared to collecting reservoir 18. For example, by making the collecting reservoirs 18 of bigger diameter than the staging reservoirs 16, the pressure head 52 decreases more slowly. By making the diameter of the reservoirs 16 and 18 large with respect to the flow rate or concentrating the polymeric molecules in the bottom of the staging reservoir 16, the molecules will pass through the micro-channel 14 only during the initial flow period providing more constant flow and transit time of the polymeric molecules 36 through the micro-channel 14.

Figure 10:
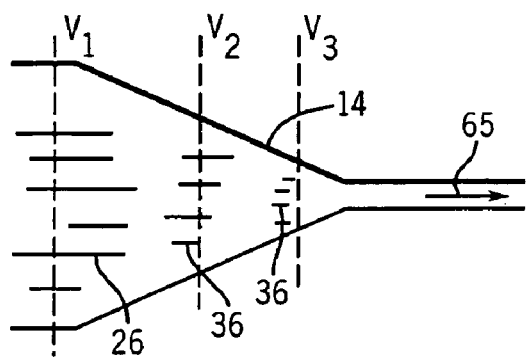
FIG. 10 is a plan view of an alternative micro-channel design providing varying cross-sections and inversely varying flow velocity such as may be used to sort polymeric molecules by size along the length of the micro-channel.

Referring now to FIG. 10 in an alternative embodiment, the micro-channel 14 may be given a varying cross-sectional area so that for a given net flow rate 65 a series of different flow velocities V1 through V3 will be created at different locations along the micro-channel 14. It is believed that these varying flow velocities may effect a spatial separation of polymeric molecules 36 according to their length. This length sorting may be desirable to separate shorter polymeric molecules 36 from overlapping with longer polymeric molecules or for analytic separation of polymeric molecules 36 by length such as currently is done with electrophoresis.

Figure 11:
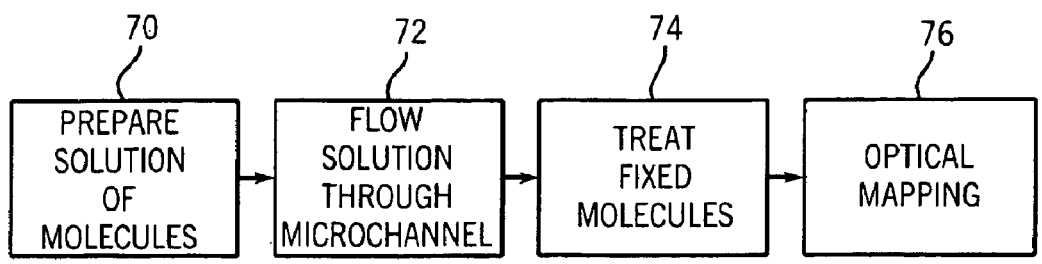
FIG. 11 is a flow diagram of the process of using the present invention to straighten and fix polymeric molecules.

Referring now to FIG. 11, the present invention may be incorporated as part of an optical mapping system. At a first step 70 of such a system, a solution, typically of water and polymeric molecules, for example, DNA, is prepared by techniques well known in the art. The polymeric molecules 36 may be treated with a condensing agent such as spermine causing them to coil, thereby reducing their damage during transfer to the apparatus 10 described above.

At step 72, the water (which will act as the carrier liquid 26) and polymeric molecules 36 are inserted into the staging reservoir 16. In the staging reservoir 16 they may be treated, for example, with a saline solution to decondense the molecules over a period, loosening their spermine-induced coiling. Once decondensed, the carrier liquid 26 and polymeric molecules 36 flow through the micro-channel 14 driven by a pump, centrifuge, or other method. During the flow, polymeric molecules 36 attach to the substrate 22 in straightened configuration.

Additional treatment of the fixed polymeric molecules 36 may be performed, as indicated by process block 74, by a variety of methods known in the art including but not limited to tagging with fluorescent materials or cutting by restriction enzymes. This step may include staining the polymeric molecules 36 with a fluorescent dye to provide accurate measurement of segments of the polymeric molecules 36.

These treatments may be performed either by passing additional liquids through the micro-channels 14 or by peeling back the channel plate 12 to allow direct access to the polymeric molecules 36 fixed to the substrate 22.

At process block 76, optical mapping of the fixed and treated polymeric molecules 36 may be performed either through the transparent optical mapping substrate 22 or by removing channel plate 12. After optical mapping, the fixed polymeric molecules 36 may be stored.

The laminar fluid flow used in the present invention, in contrast to radial or other capillary fluid flows, is believed to reduce the number of overlapping molecules. The controlled laminar flow may also provide more consistent elongation or stretching of the polymeric molecules 36. Elongation may be controlled by controlling the laminar flow velocity.

Figure 12:
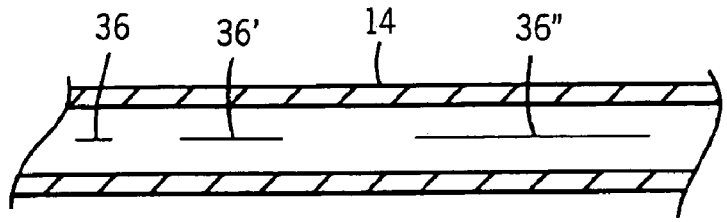
FIG. 12 is a figure similar to that of FIG. 2 showing a sorting of the elongated molecules by length and hence by molecular weight according to their different velocities within the laminar flow.

Referring now to FIG. 12, generally each polymeric molecule 36 will travel along a fixed given flow line. An important consequence of this is that long molecules of up to an inch in length are microscopically flat. This means they will stay in focus and are easily manipulated for subsequent actions including digestion by enzymes or treatment with highly focused light or laser illumination.

The flow lines in laminar flow in a rectilinear micro-channel are essentially parallel and thus the tendency of the molecules 36 to follow flow lines provides an alignment of the molecules along a common axis such as simplifies optical mapping by reducing or eliminating any crossing of the molecules 36 such as would, for example, create hot spots of florescence from two molecules 36 at the crossing juncture, or otherwise interfere with analyses of the molecules. The alignment also allows for higher density of usable molecules when affixed to a substrate or analyzed in the carrier liquid 26.

To the extent that there may be a molecular weight dependence on the particular flow line in which the molecule will settle, this effect will provide a certain spatial sorting of the molecules. This relationship between molecular weight and flow line may be one property tending to separate the molecules from one another across the channel axis and, together with the tendency for molecules to travel on a given flow line, to keep them separated as flow continues.

A sorting among molecules 36 of differing lengths may also occur to the extent that the diffusion radius 44 (described above with respect to FIG. 3) may vary as a function of molecular weight. This sorting would cause selective adsorption of the molecules 36 as a function of molecular weight and may be promoted by control of the carrier fluid flow rate and the length of the micro-channel 14 so as to increase the chance of adsorption of desired (or undesired) molecules 36 selectively.

As depicted in FIG. 12, the velocity of the molecule within the laminar flow 30 appears to have a molecular weight dependency so that the molecules 36 will sort themselves out, to some extent, by molecular weight over the length of the micro-channel 14. Thus elongated molecules 36" having greater length (and hence number of base pairs and molecular weight) may be separated axially from elongated molecules 36 and 36' having lesser length.

Figure 13:
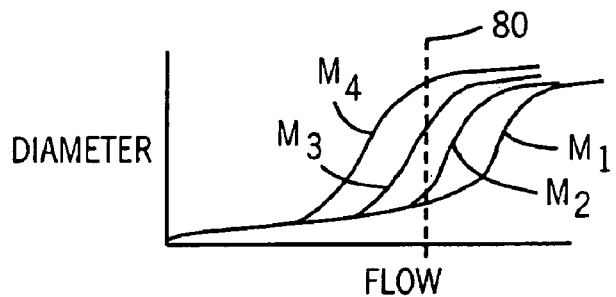
FIG. 13 is a schematic representation of a functional relationship between transition to an elongated configuration and laminar flow rate for molecules of different molecular weights serving as a basis for a second type of sorting in which molecules are selectively elongated.

Referring to FIG. 13, a second effect, believed to be present in the micro-channel 14, is a strong dependency between molecular weight and the velocity of laminar flow necessary to cause the molecules 36 to transition between a coiled configuration and an elongated configuration. Importantly, the transition from a random coil to a full elongation configuration is quite sharp as indicated by the vertical sections of the chart of FIG. 13. By selecting a given flow rate 80, for example, molecules of molecular weight $M_3$ and $M_4$ as shown by those similarly named curves will be elongated while molecules with molecular weights $M_1$ and $M_2$ will remain in a coiled configuration. Adjustment of the flow velocity allows arbitrary separations between these different molecular weights.

Figure 14:
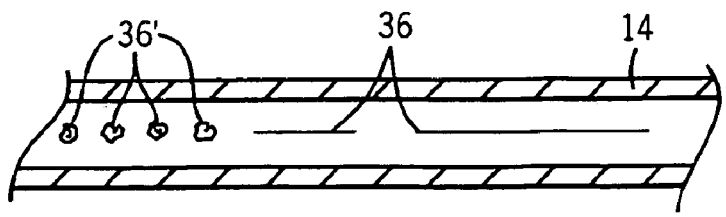
FIG. 14 is a figure similar to that of FIG. 12 showing separation of the molecules according to velocity differences caused by elongation and unelongated configurations.

Referring now to FIG. 14, by promoting the elongation of only some of the molecules 36, while leaving the other molecules 36' in coiled configuration by appropriate selection of flow velocity, a sorting of molecules by length may be performed in a manner different from that described above with respect to FIG. 12. In this case, the laminar flow 30 acts to separate the elongated molecules 36 from the coil molecules 36' making use of a difference between velocity of the molecules 36 and 36' in the laminar flow 30. Note the velocity of the flow over the length of the micro-channel 14 may be varied by changing the cross sectional area of the micro-channel 14. Thus different velocities may be used to promote elongation and separation.

Figure 15:
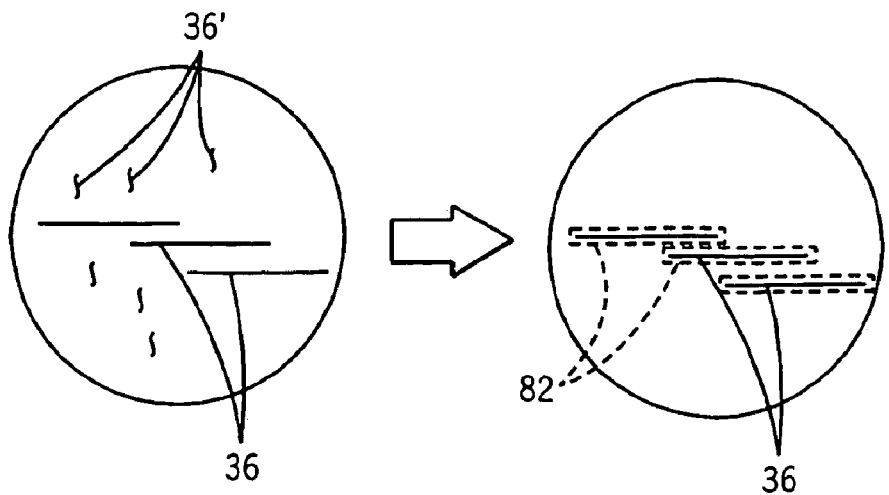
FIG. 15 is a simplified representation of two images, a first showing elongated and aligned molecules together with coiled molecules, and the second showing a separation of the aligned and elongated molecules using standard image processing techniques.

Referring now to FIG. 15, the distinction between the elongated and aligned molecules 36 and the coil molecules 36' also allow them to be readily distinguished visually. This visual difference may be exploited in an automated procedure using well known image processing techniques which produce masks 82, for example, produced using a derivative of the image values taken in the direction of the alignment, such as tends to favor aligned molecules 36 (which have high derivatives only at their ends) but to block coiled molecules 36' (which may have high derivatives) over most of their length.

Figure 16:
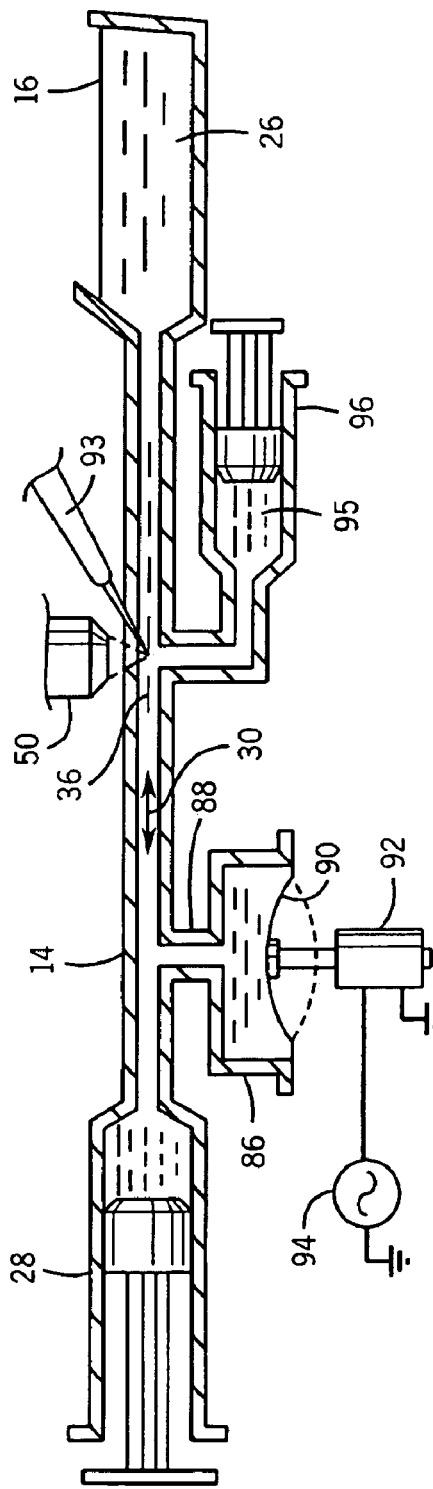
FIG. 16 is a schematic representation of a device for providing molecular hovering of molecules in a laminar flow for manipulation.

Referring now to FIG. 16, the present inventors have discovered that the molecule 36 may be encouraged to "hover" by alternating the direction of the laminar flow on a regular basis. This action essentially holds the molecule 36 in a fixed position within the micro-channel 14. One advantage to the hovering or suspension of the molecule 36 within the carrier liquid 26 is that the molecule 36 is free of surface effects that can hinder molecular assemblies and enzymatic action.

One apparatus for producing such a hovering may provide for a pump 28 such as the type described above with respect to FIG. 1 feeding the micro-channel 14, the latter that terminates in the staging reservoir 16. A microscope objective 50 may be positioned along the length of the micro-channel 14 where the hovering molecule 36 will be positioned. The microscope may be an epifluoresence microscope having an oil immersion lens and may be coupled to a camera (not shown) for recoding of the information so obtained. After the molecule is moved to this location by action of the pump 28, the pump 28 ceases and a second oscillating pump 86 is activated, the oscillating pump 86 communicating through a branch 88 with the micro-channel 14.

In this example, the oscillating pump 86 may include a diaphragm 90 that is reciprocated by a solenoid 92 connected to a sinusoidal power supply 94. A flexing of the diaphragm 90 provides for a simple, low frequency alternation of the laminar flow 30 within the micro-channel 14, preferably at a rate of 0.5 to 3 Hertz.

This ability to stabilize the molecule 36 and maintain its elongation allows complex manipulation of the molecule 36 during observation through microscope objective 50. Such manipulation may include reactions with introduced reagents 95 with and without through activation, for example, by a laser 93. The reagents 95 may be introduced using second syringe 96 communicating through an orifice with the micro-channel 14 at the site of hovering. The reagents 95 may include, for example, restriction enzymes including those activated by the laser 92 and other reactants and DNA or RNA molecules placed near the hovering molecule to promote assemblies of molecules together. These techniques may also be applied to molecules suspended in the micro-channel 14 without hovering.

Using this technique, in the case of optical mapping of nuclei acid molecules 36, as an example, the elongated, flowing nucleic acid molecules can be digested with restriction enzymes as they pass the microscope. The carrier liquid 26 can contain or have introduced restriction enzymes and each of the reagents necessary for digesting the nucleic acid molecule flowing through the chamber except that the divalent cation (usually $Mg^2+$), which is necessary for enzyme activity, is present in a reversibly chelated form. As such, the nucleic acid is protected from digestion until the divalent cations are liberated. By chelating the divalent cations with, for example, a light-inactivated chelator such as, for example, DM-nitrophen, as described below in U.S. Pat. No. 6,610,256, the cations can be released within the viewing/manipulation chamber as the fluid passes through the microscope light source.

Thus, the nucleic acid molecule 36 first becomes subject to digestion as it passes through the viewing/manipulation chamber. Further, as digestion occurs, the flow maintains the order of the resulting restriction fragments, which are imaged and which, therefore, instantly produce restriction maps which have been generated in real time. An example of such a photo-inactivated chelator is also described in U.S. Pat. No. 6,610,256.

In an alternative to holding the molecules 36 suspended in carrier liquid 26 as molecules 36 pass through the micro-channel 14, they may be adsorbed to a wall of the micro-channel 14 as has been described previously through normal action of the polymer ends under the laminar flow. Polymer ends are favored to be on the periphery of the coil molecules 36 so these sections have a high probability of attaching to the charged surfaces of the micro-channel 14.

Figure 18:
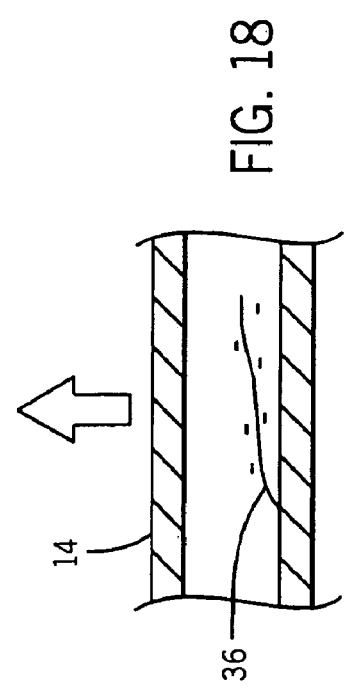
FIG. 18 is a figure similar to that of FIG. 17 showing a second method for promoting affixing of the molecules.
Figure 17:
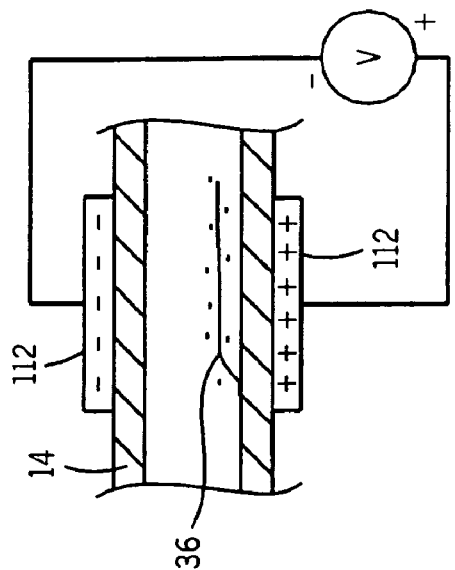
FIG. 17 is a figure similar to that of FIGS. 2, 12, and 14 showing a technique in which an electrostatic field promotes the affixing of a molecule to a wall of the micro-channel.

More precise control over the location of fixation of the molecules may be provided, for example, by using the hovering technique described above with respect to FIG. 16 and an external force for sedimentating molecules 36. As shown in FIG. 17, charged electrical plates 112 placed across micro-channel 14 may be used to impress an electrostatic field on the molecules 36 drawing the negatively charged polymeric molecule 36 to one wall. Alternatively as shown in FIG. 18, acceleration forces, for example, obtained in a centrifuge or the like, may be used to the same effect. These techniques may also be used without the necessity of putting the molecules into a hovering mode but simply as they pass by a region where fixation is desired.

The sorting techniques described above and hovering may be combined to separate molecules as desired for analyses and/or manipulation and then to allow them to re-coil again by ceasing flow. The laminar flow may then be reactivated to stretch the molecules out again. In this way, molecules 36 can be easily moved from position to position and locked into place within the fluid or affixed to a surface.

Generally, the present invention works with multiple molecules simultaneously in the micro-channel 14 and thus does not require sophisticated metering of the molecules. On the other hand, single molecules can be metered out of gel inserts per the description in U.S. Pat. No. 6,610,256. A brachiated micro-channel 14 (not shown) may be used to steer sorted or reacted molecules 36 to different locations. The methods described herein make possible the controlled, region-specific restriction digests of the elongated nucleic acid molecules which, coupled with the flow aspect of the device, makes possible the generation of real-time restriction maps.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method for elongating polymeric molecules comprising the steps of:
   (a) passing a polymeric molecule in a laminar-flowing liquid through a micro-channel sized to provide laminar flow having liquid flow lines all substantially parallel to each other along a full length of the micro-channel; and
   (b) controlling the flow of the liquid to cause elongation of the polymeric molecule within the laminar flow; and
   (c) periodically reversing the laminar flow to cause the polymeric molecule to hover in an elongated state.

2. The elongation method of claim 1 wherein the micro-channel has a cross-sectional dimension within one order of magnitude of a relaxed diameter of the polymeric molecule.

3. The elongation method of claim 1 wherein the micro-channel includes a transparent wall and including the step of optically analyzing the elongated polymeric molecule suspended within the laminar flow.

4. The elongation method of claim 1 including the step of reacting the elongated polymeric molecule suspended within the laminar flow with a reactant.

5. The elongation method of claim 4 wherein the reactant is an enzyme causing cleavage of the polymeric molecule.

6. The elongation method of claim 4 wherein the reactant is a second polymeric molecule reacting with at least one elongated polymeric molecule.

7. The elongation method of claim 6 wherein the polymeric molecules are DNA.

8. The elongation method of claim 1 wherein multiple polymeric molecules are simultaneously passed through the channel.

9. The elongation method of claim 1 including the step of staging the polymeric molecule with a plurality of other polymeric molecules in the liquid before passage through the channel.

10. The elongation method of claim 1 wherein the laminar flow is periodically reversed at a rate from between 0.2-5 Hz.

11. The elongation method of claim 1 wherein the micro-channel includes a transparent wall and including the step of optically analyzing the elongated polymeric molecule as it hovers within the laminar flow.

12. The elongation method of claim 1 including the step of reacting the elongated polymeric molecule hovering within the laminar flow with a reactant.

13. The elongation method of claim 12 wherein the reactant is an enzyme causing cleavage of the polymeric molecule.

14. The elongation method of claim 12 wherein the reactant is a second polymeric molecule.

15. The elongation method of claim 14 wherein the polymeric molecules are DNA.

16. The elongation method of claim 1 wherein at least a first wall of the micro-channel provides attraction to the polymeric molecule and further including the step of:
   (d) adsorbing of the polymeric molecule to the first wall of the micro-channel in straightened form.

17. The elongation method of claim 16 wherein step (c) includes the steps of controlling the flow rate of the liquid and the size of the micro-channel to cause adsorption by random encounters between at least one end of the polymeric molecule and a wall of the micro-channel.

18. The elongation method of claim 16 wherein step (c) includes the step of applying a centrifugal acceleration across the width of the micro-channel to cause adsorption of the polymeric molecule to one wall of the micro-channel.

19. The elongation method of claim 16 wherein step (c) includes the step of applying an electrostatic field across the width of the micro-channel to cause adsorption of the polymeric molecule to one wall of the micro-channel.

20. The elongation method of claim 16 wherein the micro-channel includes an elastic channel material releasably adhered to an optical mapping surface to create the micro-channel between the elastic material and the optical mapping surface; and wherein the adsorption is to the optical mapping surface.

21. The elongation method of claim 20 further including the step of separating the elastic channel material from the optical mapping surface after adsorption of the polymeric molecule to the optical mapping surface.

22. The elongation method of claim 16 further including the step of reacting the adsorbed polymeric molecule with a reactant.

23. The elongation method of claim 22 wherein the reactant is an enzyme causing cleavage of the polymeric molecule.

24. A method for aligning polymeric molecules comprising the steps of:
(a) passing a plurality of polymeric molecules in a laminar-flowing liquid through a micro-channel sized to provide laminar flow having liquid flow lines all substantially parallel to each other along a full length of the micro-channel; and
(b) controlling the flow of the liquid to cause alignment of the polymeric molecules within the laminar flow; and
(c) periodically reversing the laminar flow to cause the polymeric molecule to hover in an elongated state.

25. The alignment method of claim 24 wherein the micro-channel has a cross-sectional dimension within one order of magnitude of a relaxed diameter of the longest polymeric molecule.

26. The alignment method of claim 24 wherein the micro-channel includes a transparent wall and including the step of optically analyzing the aligned polymeric molecules suspended within the laminar flow.

27. The alignment method of claim 24 including the step of reacting the aligned polymeric molecules suspended within the laminar flow with a reactant.

28. The alignment method of claim 27 wherein the reactant is an enzyme causing cleavage of the polymeric molecules.

29. The alignment method of claim 27 wherein the reactant is a second polymeric molecule reacting with at least one aligned polymeric molecule.

30. The alignment method of claim 24 wherein the polymeric molecules are DNA.

31. The alignment method of claim 24 wherein the laminar flow is periodically reversed at a rate from between 0.2-5 Hz.

32. The alignment method of claim 24 wherein the micro-channel includes a transparent wall and including the step of optically analyzing the aligned polymeric molecules as they hover within the laminar flow.

33. The alignment method of claim 24 including the step of reacting the aligned polymeric molecules hovering within the laminar flow with a reactant.

34. The alignment method of claim 33 wherein the reactant is an enzyme causing cleavage of the polymeric molecules.

35. The alignment method of claim 33 wherein the reactant is a second polymeric molecule.

36. The alignment method of claim 33 wherein the polymeric molecules are DNA.

37. The alignment method of claim 24 wherein at least a first wall of the micro-channel provides attraction to the polymeric molecules and further including the step of:
(d) adsorbing of the polymeric molecules to the first wall of the micro-channel in aligned form.

38. The alignment method of claim 37 wherein step (c) includes the steps of controlling the flow rate of the liquid and the size of the micro-channel to cause adsorption by random encounters between at least one end of the polymeric molecules and a wall of the micro-channel.

39. The alignment method of claim 37 wherein step (c) includes the step of applying a centrifugal acceleration across the width of the micro-channel to cause adsorption of the polymeric molecules to one wall of the micro-channel.

40. The alignment method of claim 37 wherein step (c) includes the step of applying an electrostatic field across the width of the micro-channel to cause adsorption of the polymeric molecules to one wall of the micro-channel.

41. The alignment method of claim 37 wherein the micro-channel includes an elastic channel material releasably adhered to an optical mapping surface to create the micro-channel between the elastic material and the optical mapping surface;
and wherein the adsorption is to the optical mapping surface.

42. The alignment method of claim 41 further including the step of separating the elastic channel material from the optical mapping surface after adsorption of the polymeric molecules to the optical mapping surface.

43. The alignment method of claim 37 further including the step of reacting the adsorbed polymeric molecules with a reactant.

44. The alignment method of claim 43 wherein the reactant is an enzyme causing cleavage of the polymeric molecules.

45. The alignment method of claim 24 wherein the micro-channel includes a transparent wall and including the step of optically analyzing the aligned polymeric molecules within the laminar flow.

46. A method for separating polymeric molecules of differing molecular weight comprising the steps of:
(a) passing polymeric molecules in a laminar-flowing liquid through a micro-channel sized to provide laminar flow having liquid flow lines all substantially parallel to each other along a full length of the micro-channel; and
(b) controlling the laminar flow of the liquid to separate the polymeric molecules by differing molecular weights within the laminar flow; and
(c) periodically reversing the laminar flow to cause the polymeric molecule to hover in an elongated state.

47. The separation method of claim 46 further including the step of controlling the flow of liquid to elongate the molecules and separate the elongated molecules by their relative speeds within the laminar flow.

48. The separation method of claim 46 wherein the laminar flow is periodically reversed at a rate from between 0.2-5 Hz.

49. The separation method of claim 46 wherein the micro-channel includes a transparent wall and including the step of optically analyzing the separated polymeric molecules as they hover within the laminar flow.

50. The separation method of claim 46 including the step of reacting the separated polymeric molecules hovering within the laminar flow with a reactant.

51. The separation method of claim 50 wherein the reactant is an enzyme causing cleavage of at least one polymeric molecule.

52. The separation method of claim 50 wherein the reactant is a second polymeric molecule.

53. The separation method of claim 52 wherein the polymeric molecules are DNA.

54. The separation method of claim 47 further including the step of fixing the separated polymeric molecules to a substrate after their separation.

55. The separation method of claim 54 wherein the microchannel includes an elastic channel material releasably adhered to an optical mapping surface to create the microchannel between the elastic material and the optical mapping surface;

and separated polymeric molecules are fixed to the optical mapping surface.

56. The separation method of claim 55 further including the step of separating the elastic channel material from the optical mapping surface after adsorption of the polymeric molecule to the optical mapping surface.

57. The separation method of claim 54 further including the step of reacting the adsorbed polymeric molecule with a reactant.

58. The separation method of claim 57 wherein the reactant is an enzyme causing cleavage of the polymeric molecule.

59. The separation method of claim 57 wherein the reactant is a second polymeric molecule reacting with at least one elongated polymeric molecule.

60. The separation method of claim 54 wherein the polymeric molecules are DNA.

61. The separation method of claim 46 wherein the microchannel includes a transparent wall and including the step of optically analyzing the sorted polymeric molecule suspended within the laminar flow.

62. The separation method of claim 46 further including the step of controlling the flow of liquid to cause elongation only of the polymeric molecules of a predetermined molecular weight range within the laminar flow.

63. The separation method of claim 62 further including the step of fixing the elongated polymeric molecules to a substrate.

64. The separation method of claim 62 further including the step of controlling the flow of liquid to separate the elongated and unelongated molecules as a function of their differing speed within the laminar flow and to separate the elongated molecules from the unelongated molecules by their different speeds in the laminar flow.

65. The separation method of claim 62 further including the step of obtaining a digital image of the elongated and unelongated molecules and separating them by image processing.

66. The separation method of claim 46 wherein the microchannel has a cross-sectional dimension within one order of magnitude of a relaxed diameter of the polymeric molecule.

67. The separation method of claim 46 further including the step of controlling the flow of liquid to separate the molecules as a function of their propensity to be adsorbed as a function of their length while moving in the laminar flow.

* * * * *